United States Patent
Burn et al.

(10) Patent No.: US 7,740,954 B2
(45) Date of Patent: Jun. 22, 2010

(54) REACTIVE DENDRIMERS

(75) Inventors: Paul Leslie Burn, Oxford (GB); Ifor David William Samuel, Fife (GB); Michael Frampton, Oxford (GB)

(73) Assignees: Isis Innovation Limited, Oxford (GB); The University Court Of The University Of St. Andrews, Fife (GB)

( * ) Notice: Subject to any disclaimer, the term of this patent is extended or adjusted under 35 U.S.C. 154(b) by 638 days.

(21) Appl. No.: 10/485,799

(22) PCT Filed: Aug. 27, 2003

(86) PCT No.: PCT/GB03/03713

§ 371 (c)(1),
(2), (4) Date: Mar. 30, 2005

(87) PCT Pub. No.: WO2004/020547

PCT Pub. Date: Mar. 11, 2004

(65) Prior Publication Data

US 2005/0164029 A1     Jul. 28, 2005

(30) Foreign Application Priority Data

Aug. 29, 2002  (GB) .................................. 0220092.1

(51) Int. Cl.
*B32B 9/00* (2006.01)
*C08G 83/00* (2006.01)
(52) U.S. Cl. .................. 428/690; 428/917; 525/242
(58) Field of Classification Search .................. 428/690, 428/917; 525/242
See application file for complete search history.

(56) References Cited

FOREIGN PATENT DOCUMENTS

| JP | 2000-219707 | 8/2000 |
|---|---|---|
| WO | WO 93/12073 | 6/1993 |
| WO | WO 95/02008 | 1/1995 |
| WO | WO 97/23514 | 7/1997 |
| WO | WO 99/21935 | 5/1999 |
| WO | WO 99/48898 | 9/1999 |
| WO | WO 01/59030 | 8/2001 |
| WO | WO 02/066552 | 8/2002 |
| WO | WO 02/066575 | 8/2002 |
| WO | WO 02/067343 | 8/2002 |
| WO | WO 03/079736 | 9/2003 |

OTHER PUBLICATIONS

J. Lupton et al., Control of Electrophosphorescence in Conjugated Dendrimer Light-Emitting Diodes, 11 Advanced Functional Materials 287-294 (2001).
J. Markham et al., High-Efficiency Green Phosphorescence From Spin-Coated Single-Layer Dendrimer Light-Emitting Diodes, 15 Applied Physics Letters 2645-2647 (2002).
J. Pillow et al., A Facile Iterative Procedure for the Preparation of Dendrimers Containing Luminescent Cores and Stilbene Dendrons, 32 Macromolecules 5985-5993 (1999).
M. Watson et al., Big Is Beautiful—"Aromaticity" Revised From the Viewpoint of Macromolecular and Supramolecular Benzene Chemistry, 101 Chem. Rev. 1267-1300 (2001).

(Continued)

*Primary Examiner*—Duc Truong
(74) *Attorney, Agent, or Firm*—Quarles & Brady LLP

(57) ABSTRACT

A process for modifying at least one dendron that is intended to form part of a dendrimer is disclosed. One reacts at least one reactable unsaturated group in a chemoselective manner to form a less unsaturated group. Also disclosed is a process for modifying dendrimers in a similar manner.

26 Claims, 6 Drawing Sheets

▽ Branching unit
☐ Core
○ Surface group

Dendrimer A of generation 2

Dendrimer B of generation 3

OTHER PUBLICATIONS

S. Lo et al., Green Phosphorescent Dendrimer for Light-Emitting Diodes, 13 Adv. Mater. 975-979 (2002).

Z. Bo et al., Synthesis of Low-Generation, Aryl-/Alkyl-Type, Nonpolar Dendrons Carrying Protected Hydroxyalkly Groups in the Periphery, 67 J. Org. Chem. 5327-5332 (2002).

Pei-Wei Wang et al., Electroluminescent Diodes From a Single-Component Emitting Layer of Dendritic Macromolecules, 8 Adv. Mater. 237-241 (1996).

M. Halim et al., Conjugated Dendrimers for Light-Emitting Diodes: Effect of Generation, 11 Adv. Mater. 371-374 (1999).

A. Freeman et al., Dendrimer-Containing Light-Emitting Diodes: Toward Site-Isolation of Chromophores, 122 J. Am. Chem. Soc. 12385-12386 (2000).

A. Adronov et al., Light-Harvesting Dendrimers, Chem. Commun. 1701-1710 (2000).

C. Kwok et al., Synthesis and Light-Emitting Properties of Difunctional Dendritic Distyrylstilbenes, 34 Macromolecules 6821-6830 (2001).

J. Lupton et al., Control of Mobility in molecular Organic Semiconductors by Dendrimer Generation, 63 Physical Review B 155206-1-155206-8 (2001).

R. Crooks et al., Dendrimer-Encapsulated Metals and Semiconductors: synthesis, Characterization, and Applications, Topics in Current Chemistry, Dendrimers III, 81-135, Springer-Verlag, Berlin Heidelberg, (2001).

An examination report in a counterpart Japanese application 2004-532291, the report being mailed Jun. 16, 2009, together with an English translation thereof.

▽ Branching unit
☐ Core
○ Surface group

Dendrimer A of generation 2    Dendrimer B of generation 3

BG = branching group

REACTIVE DENDRIMERS

This application claims priority on GB0220092.1 filed on Aug. 29, 2002 and PCT/GB2003/003713 filed on Aug. 27, 2003.

This invention relates to a process for forming dendrons and dendrimers and their use in opto-electric devices.

BACKGROUND

Dendrimers are branched macromolecules with a core and attached dendrons, also known as dendrites. Dendrons are branched structures comprising branching units and optionally linking units. The generation of a dendron is defined by the number of sets of branching groups; see FIG. 1. Dendrons with the same structure (architecture) but a higher generation, or order, are composed of the same structural units (branching and linking units) but have an additional level of branching. There can be surface groups on the periphery or distal units of the dendrons.

Dendrimers of different generations can have different types of branching points and linking units. Dendrimers are generally synthesised by convergent or divergent routes. Convergent routes require a functional group at the dendron foci which can either be reacted directly to give a higher generation dendron or dendrimer or activated before the reaction to form a higher generation dendron or dendrimer. For divergent routes the distal functional groups are used, either after activation or directly, to form the next higher generation dendrimer. Once the dendrimer is formed it has been demonstrated that the surface groups can be modified, e.g. t-butylcarbonates can be removed to leave hydroxyl moieties. The linking, branching, and core units of a dendrimer can either be made up of saturated or unsaturated units. The presence of unsaturated units within a dendron or dendrimer gives rise to the possibility of modifying the structure to form a final dendrimer that has beneficial properties and which could not be formed easily by another method. In particular this invention pertains to a chemical conversion of one or more unsaturated units within a dendron or dendrimer to give bonds which are more saturated between the atoms within the unit. The process is different from other reported reactions of unsaturated units. For example it has previously been shown that when di-substituted vinylene units are present within a dendrimer they can be isomerised (see J. N. G. Pillow et al, *Macromolecules*, 1999, 32, 5985). Although this is a chemical transformation it does not change the level of saturation and therefore falls outside the scope of this invention. In addition, it has been reported that phenylene based dendrimers have been oxidised to form graphite like structures (FIG. 8A illustrates one component of a dendrimer) (M. D. Watson et al, *Chem. Rev.*, 2001, 101, 1267). Although this is a reaction within the dendron and/or dendrimer structure it does not constitute a reduction in the level of saturation of the $sp^2$ hybridised carbons of the benzene rings. In this case the carbon-proton bond is merely converted to a carbon-carbon bond. Similarly di-dendroned substituted 4,4'-diphenylacetylene dendrons have been cyclised to form larger benzene centered dendrimers (M. D. Watson et al, *Chem. Rev.*, 2001, 101, 1267). The starting material in FIG. 8B is a dendron where the acetylene unit is the focus with two dendrons attached. The foci of three of these dendrons react to form the central benzene unit of the dendrimer and the other components of the dendrons are unchanged. Recently dendrimers that have unsaturated units have been shown to be useful as the light emitting-layer in organic light-emitting diodes.

Organic light-emitting diodes (OLEDs), also known as organic electroluminescent (EL) devices, are an emerging display technology. In essence an OLED comprises a thin organic layer or stack of organic layers sandwiched between two electrodes, such that when a voltage is applied visible or other light is emitted. At least one of the electrodes must be transparent to light. For display applications the light must of course be visible to the eye, and therefore at least one of the electrodes must be transparent to visible light.

There are two principal techniques that can be used to deposit the organic layers in an OLED: thermal evaporation and solution processing. Solution processing has the potential to be the lower cost technique due to its potentially greater throughput and ability to handle large substrate sizes. Significant work has been undertaken to develop appropriate materials, particularly polymers. More recently dendrimers that are photoluminescent in the solid state have been shown to have great promise as solution processible light-emitting materials in OLEDs (S.-C. Lo, et al *Adv. Mater.*, 2002, 13, 975; J. P. J., Markham, et al *Appl. Phys. Lett.*, 2002, 80, 2645).

Light-emitting dendrimers typically have a luminescent core and in many cases an inherently at least partially conjugated dendrons. As used herein, an inherently at least partially conjugated dendritic structure is one in which there is conjugation between the groups making up the dendritic structure, but the pi-system is not necessarily fully delocalised. The delocalisation of the pi-system is dependent on the regiochemistry of the attachment of the different groups. Such dendrons can also be conjugated dendrons. Further examples of light-emitting dendrimers include those found in P. W. Wang, et al *Adv. Mater.*, 1996, 8, 237; M. Halim, et al *Adv. Mater.*, 1999, 11, 371; A. W. Freeman, et al *J. Am. Chem. Soc.*, 2000, 122, 12385; A. Adronov, et al *Chem. Comm.*, 2000, 1701; C. C. Kwok, et al *Macromolecules*, 2001, 34, 6821. Light-emitting dendrimers have the advantage over light-emitting polymers that the light-emitting properties and the processing properties can be independently optimised as the nature of the core, dendrons and surface groups can be independently altered. For example with dendrimers that contain light-emitting cores the emission colour of the dendrimer can be changed by simply changing the core. Although dendrimers with a light-emitting core are preferred, when the core is not luminescent the chromophores in the dendron can be light-emitting.

Other physical properties, such as viscosity, may also make dendrimers more easily tailored to the available manufacturing processes than polymers. Organometallic dendrimers have previously been used in OLED applications as a single component in a film (i.e. a neat film) or in a blend with a molecular material or in a blend of more than one dendrimer of different type (i.e. different cores), e.g. J. M. Lupton et al. *Adv. Funct. Mater.*, 2001, 11, 287 and J. P. J., Markham, et al *Appl. Phys. Lett.*, 2002, 80, 2645.

Intermolecular interactions play an important role in the opto-electronic properties of organic light-emitting and transport materials. Close contact and good order can lead to high charge mobilities but can also give rise to reduced emission due to the formation of excited-state dimers. In previous work we have shown that intermolecular interactions can be controlled by the generation of the dendrons attached to a dendrimer (J. M. Lupton, et al *Phys. Rev. B*, 2001, 63, 5206; J. P. J., Markham, et al *Appl. Phys. Lett.*, 2002, 80, 2645). However the nature of the intermolecular interactions is affected by the type of dendron that is attached to the core. Generally, when the dendrimers are prepared via a convergent or divergent route the main structure of the final dendrimer is defined by the dendron branching groups and linking units used in the synthesis. This gives a limitation over the control of the dendrimer architecture and properties. Within a dendron or dendrimer there is potential for the surface groups, branching groups and linking units, where present, and foci in the case of dendrons, and core in the case of dendrimers, to be modified. It is known that surface groups of dendrimers and dendrons and the foci of dendrons can be modified. However, as many dendrimers contain saturated linking units and branching groups the modification of these units can be difficult. In contrast dendrons or dendrimers containing unsaturated units within the linking units and branching groups of the dendrons and the core offer an unexpected advantage for modifying the dendron and dendrimer structures. This is different from the reactions used in the divergent or convergent route where a surface or focal group that contains unsaturation is converted into a surface group for further generation building. For example, in a divergent route the surface groups of the lower generation are typically activated to make them reactive to the species added in the next stage. This is illustrated in the synthesis of poly(iminopropane-1,3-diyl) (PPI) dendrimers which are formed by the Michael addition of acrylonitrile to 1,4-diaminobutane. After the addition the resultant terminal nitrile groups are reduced to form the primary amine terminated first generation dendrimer, which can then be reacted with more equivalents of acrylonitrile. The reduction is repeated to form the next generation dendrimer (Topics in Current Chemistry, Dendrimers III, p 86, Springer-Verlag, Berlin Heidelberg, 2001). This approach is different from that of the current invention, in which the entire dendron or dendrimer structure is built such that it contains unsaturated units within the branching groups and/or linking units and/or core, and then the dendron or dendrimer is modified by reaction of some or all of said units. In particular unsaturated groups such as acetylenyl and vinyl groups within the dendron of a dendrimer are reacted. With this method we have been able to produce dendrimers with aryl branching groups linked by ethylene units using the powerful Pd catalysed coupling of aryl halides and alkenes, followed by simple hydrogenation. In contrast, previous routes to saturated links between aromatic branching groups have involved a complex series of reactions where the hydrocarbon linking unit is introduced via a number of steps prior to the Pd coupling to form the dendrimer (Z. Bo, A. D. Schlüter *J. Org. Chem.* 2002, 67, 5327). A further advantage of this invention is that it gives additional flexibility in the choice of end product. After the coupling to form the unsaturated unit a range of reactions, such as halogenation and hydrogenation of alkenes and acetylenes can be used to give a variety of alternative products from the same intermediate material. We have discovered that by using dendrons that contain acetylene and vinylene links between branching points in dendrons and further reacting them it gives a way of advantageously modifying the dendrons and hence the dendrimers.

SUMMARY OF THE CURRENT INVENTION

The present invention is thus directed at overcoming limitations in the synthetic procedures for the formation of dendrons and dendrimers with saturated units in the dendrons and/or core, and their use in opto-electronic devices, in particular OLEDs.

According to the present invention there is provided a process for modifying at least one dendron intended to form part of a dendrimer, said dendron having the formula:

FO(dendrite–$Q_a$)$_y$                                            (I)

wherein FO is a functional group attached, either directly or via a linking group which can contain one or more reactable unsaturated units, to the first branching atom or group of the dendrite, each "dendrite" which may be the same or different is a dendrite which contains branching atoms or groups and optionally linking groups and comprises at least said first branching atom or group which must have, in addition to FO (either directly or via a linking group), 2 or more groups attached and in which the distal group of each arm of the dendrite is an aryl or heteroaryl group, at least one of said dendrite or, if present, the linking group to FO containing one or more reactable unsaturated units, y is 1 or more, Q is a surface group and a is 0 or an integer, which comprises reacting at least one said reactable unsaturated group in a chemoselective manner to form a less unsaturated group.

When a is 0 there are no surface groups but preferably a is an integer, generally from 1 to 16.

The present invention also provides a process for modifying a dendrimer of the formula:

CORE–[dendrite–$Q_a$]$_x$ wherein Q and a are as defined above, x is one or 2 or more such that when x is more than one each dendrite–$Q_a$ can be the same or different and CORE represents an atom or group and CORE terminates at the single bond to the first branching atom or group in the or each dendrite, each "dendrite" which may be the same or different is a dendrite which contains branching atoms or groups and optionally linking groups, at least one of CORE and "dendrite" comprising at least one reactable unsaturated group, provided that the distal group of each arm of the or each dendrite is an aryl or heteroaryl group, which comprises reacting at least one reactable unsaturated group to form a less unsaturated group in a chemoselective manner e.g. while leaving Q unchanged.

The present invention also provides a process for making a dendrimer which involves reacting at least one dendron with a dendrimer precursor wherein the dendron is one which has been modified by a process of this invention. Such a process can be carried out in conventional manner whereby the functional group, FO, of the dendron reacts with the dendrimer precursor. By "functional group" as used herein is meant a group which is capable of reacting, either directly or after activation, with one or more other molecules, such that optionally after attachment of one or more further dendrons, a dendrimer is formed via a convergent route. In general FO and Q should be such that they can be reacted independently; they will therefore not be the same. The functional group of the dendron, FO, can, in the resulting dendrimer, form part of the core. The functional group, FO, can be one of two types. In one case it is a simple functional group such as an alcohol, halide, aldehyde or boronic acid group which can react with other moieties to form a dendrimer. In these cases the functional group may no longer be present in the final dendrimer. For example, aldehyde-focused dendrons react with pyrrole to form a porphyrin core with dendrons attached. The aldehyde itself is no longer present, but the carbon atom of the aldehyde forms part of the porphyrin core. Alternatively the functional group can be a more complex group consisting of a number of components e.g. one or more (hetero)aryl rings. If, for example, the core is organometallic then the functional group can be a ligand which is reacted with a metal cation to form the dendrimer. In this case, in the reaction to form the dendrimer, the functional group becomes part of the core but is still readily identifiable as the starting moiety. For example dendrons linked to a 2-phenylpyridine functional group react with an iridium cation to form iridium based dendritic complexes with 2-phenylpyridine as part of the core. The functional group may require activation, e.g. deprotection or transformation into another type of functional group, before it will react with the other molecule to form a dendrimer. However, it is the functional group that is at the foci, and not the link between FO and the first branching atom or group in the dendrite that is used to form the dendrimer. When FO is attached to dendrite via a linking unit the backbone of the linking unit is comprised of only sp and/or $sp^2$ hybridised atoms (before modification). The other reactive moieties that react with the dendrons to form the dendrimers, such as pyrrole or iridium trichloride in the examples mentioned above, are viewed as dendrimer precursors. One or more dendrimer precursors may be involved in forming the dendrimer.

Particularly with an organometallic dendrimer, y can be more than one; for example with a bicyclic ligand such as phenyl-pyridyl a dendrite can be attached to each ring.

DETAILED DESCRIPTION OF THE CURRENT INVENTION

The present invention is directed towards modifying unsaturated groups including vinylene, acetylenyl, imino, azo or vinylnitrile units within a dendrite or CORE either before reaction to form a dendrimer or as part of a dendrimer, the dendrimers that have been made by this process and the subsequent use of these dendrimers in opto-electronic devices and in particular OLEDs.

Figure 1:
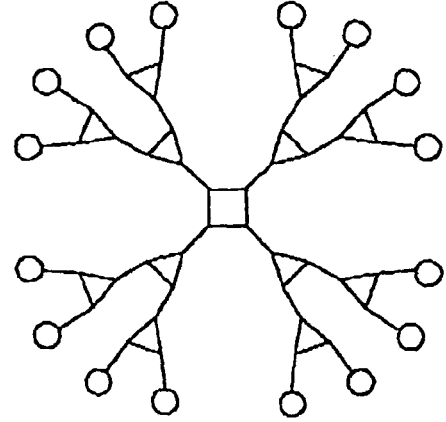
FIG. 1 shows how the generation of a dendron is defined by the number of sets of branching groups.
Figure 1:
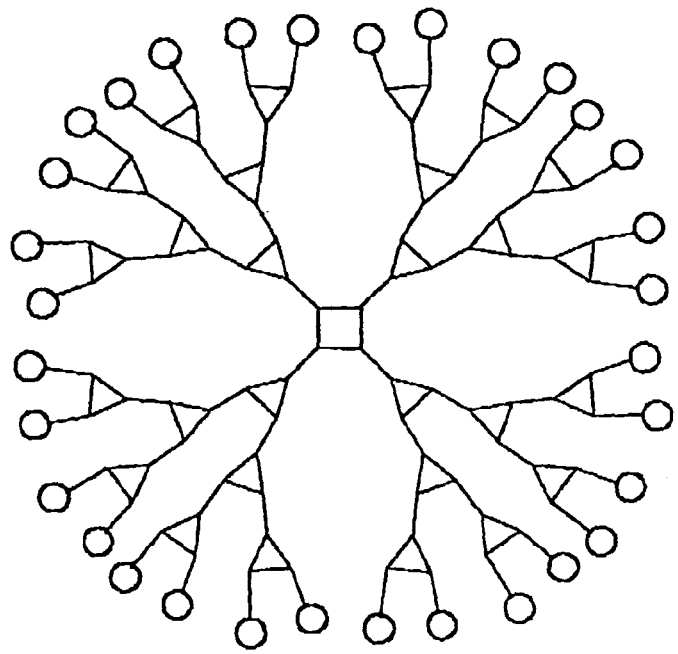
Figure 2:
FIG. 2 shows that dendrons or dendrimers that can be considered for modification must contain at least one unsaturated group (the reactable group) within the dendron or dendrimer, which are not surface groups, and that can be further reacted.
Figure 2:
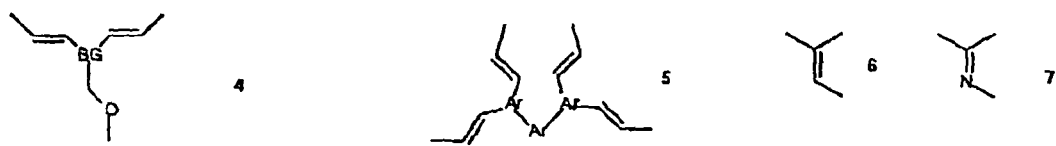

There are several types of dendrons or dendrimers that can be considered for modification but all must contain at least one unsaturated group (the reactable group) within the dendron or dendrimer, which are not surface groups, and that can be further reacted (FIG. 2). These reactable groups, which can form a branching point as in the case of 6 and 7 (see FIG. 2), are groups that are capable of undergoing reactions to form more saturated and preferably fully saturated bonds between the atoms. For example, an acetylene bond could be reduced under Lindlar's conditions to a vinylene or using hydrogen and palladium on charcoal to form an ethylene. A chemoselective reaction is one in which only the reactable unsaturated groups in the molecule undergo the reaction and the other groups in the molecule, including FO (if present) and all Q, are unchanged by the reaction. The branching points of the dendrite can either be an atom such as nitrogen or a group, but are preferably an aryl or heteroaryl where aryl and heteroaryl can also form part of a fused ring system. More preferably the branching unit is a 1,3,5 substituted benzene or 3,6,N-substituted carbazolyl group. Typically the reactive group is vinylene or acetylene and in a dendrimer either forms the links between all branching groups of the dendrite or forms the part of the core directly bonded to the first branching point of the dendrite or is a link between the last branching group of the dendrite and the distal, aryl, group of the dendrite. In one embodiment the, or each, dendrite in the dendron contains at least one reactable unsaturated group. In a second embodiment the dendrite contains the only reactive unsaturated group. In another embodiment the, or each, linking group between FO and the first branching point of the dendrite contains the only reactable unsaturated groups in the dendron. In a further embodiment, the CORE contains the only reactable unsaturated groups in the dendrimer. The links between the branching points (BG in FIG. 2) can all be of one type, e.g. acetylenyl as in 1 in FIG. 2, vinyl as in 2, or a mixture as in 3. It is preferred that only non-aryl groups are reacted. For 1, 2, and 3 one or more of the unsaturated links can be converted, depending on the number of equivalents of reagents, according to the process of this invention into a saturated link; this may give rise to a mixture of dendrons or dendrimers. It is preferred that all the equivalent unsaturated groups are reacted. For example, if vinylene units are present then they are all reacted. In 4 the branching moiety has two vinylene and one methylenoxy linking unit; the two alkene groups can be converted. An alternative asymmetric dendrimer type is one having a mixture of alkenyl, acetylenyl and aryl-aryl bonds in the dendrons. 5 illustrates an example of the alkenyl and aryl case. It is preferred that in this case only the alkenyl and acetylenyl groups react. One of the branching points can also be considered to be the unsaturated carbon atom as in the case of the vinylene 6 and imine 7 units. Preferably in the case that all the links between the branch points are reactive they are comprised of vinyl or acetylenyl or a combination of the two. In general the backbone of the linking group(s) is only comprised of sp and/or $sp^2$ hybridised atoms. The combination of vinyl and acetylene with aryl and heteroaryl branches and aryl-aryl links of which 5 is an example is also preferred. Preferred units include phenyl-vinyl-phenyl and phenyl-acetylenyl-phenyl. It is especially preferred that the branching group is (hetero)aryl which remains unchanged when unsaturated groups are reacted e.g. hydrogenated. It will be appreciated that there can be different numbers and combinations of conjugated units between branching points. The reaction of vinyl, acetylenyl or iminyl groups to give saturated units removes the conjugation and potentially introduces new functionality. In a preferred embodiment the unsaturated group becomes fully saturated. In some cases the new functionality can be further reacted, e.g. in cross-linking reactions. For example, addition of hydrogen bromide to a vinylene unit between two phenyl groups in the dendron would give rise to a benzylic bromide which could be substituted by a range nucleophiles such as alcohols. Where a diol is used two dendrons or dendrimers could be covalently linked together. It will be appreciated that a linking unit may have more than one unsaturated unit capable of reaction. For example, there may be a divinylbenzene link between two phenyl branch points.

Examples of dendrons and dendrimers which can be subjected to the process of this invention include dendrimers which have at least one inherently partially conjugated dendron such as those described in WO99/21935 for example those of formula (A):

$$\text{CORE-[DENDRITE]}_n \quad (A)$$

in which CORE represents an atom or group, n represents an integer of at least 1 and DENDRITE, which may be the same or different if n is greater than 1, represents an inherently at least partly conjugated dendritic molecular structure comprising aryl and/or heteroaryl groups and alkenyl groups connected to each other via a carbon atom of an alkenyl group to a ring carbon atom of an aryl or heteroaryl group, CORE terminating in the first single bond which is connected to a ring carbon atom of an (hetero)aryl group to which more than one at least partly conjugated dendritic chain is attached, said ring carbon atom forming part of DENDRITE, the CORE and/or DENDRITE being luminescent, including ones where the dendrons are not all the same as disclosed in PCT/GB02/00765, in general those having the formula (B):

$$\text{CORE-[DENDRITE}^1]_n[\text{DENDRITE}^2]_m \quad (B)$$

in which CORE represents an atom or group, n and m, which may be the same or different, each represent an integer of at least 1, each DENDRITE¹, which may be the same or different when n is greater than 1, and each DENDRITE², which may be the same or different when m is greater than 1, represent dendritic structures, at least one of said structures being fully conjugated and comprising aryl and/or heteroaryl groups and, optionally, vinyl and/or acetylenyl groups, connected via sp² or sp hybridized carbon atoms of said (hetero) aryl, vinyl and acetylenyl groups, and at least one branching point and/or link between the branching points in DENDRITE¹ being different from those in DENDRITE², CORE terminating in the single bond which is connected to a sp² hybridized (ring) carbon atom of the first (hetero)aryl group to which more than one conjugated dendritic branch is attached, said ring carbon atom forming part of said fully conjugated DENDRITE¹ or DENDRITE² and CORE terminating at the single bond to the first branching point for the other of said DENDRITE¹ or DENDRITE², at least one of the CORE, DENDRITE¹ and DENDRITE² being luminescent, and those of formula (C):

$$\text{CORE-[DENDRITE]}_n \quad (C)$$

in which CORE represents an atom or group, n represents an integer of at least 1, each DENDRITE, which may be the same or different, represents an inherently at least partially conjugated dendritic molecular structure which comprises aryl and/or heteroaryl and, optionally, vinyl and/or acetylenyl groups, connected via sp² or sp hybridized carbon atoms of said (hetero) aryl, vinyl and acetylenyl groups, and wherein the links between adjacent branching points in said DENDRITE are not all the same, CORE terminating in the single bond which is connected to a sp² hybridized (ring) carbon atom of the first (hetero)aryl group to which more than one dendritic branch is attached, said ring carbon atom forming part of said DENDRITE, the CORE and/or DENDRITE being luminescent and ones where the dendrons comprise aryl-aryl ligands and branching points as disclosed in PCT/GB02/00739, in general those having the formula (D):

$$\text{CORE-[DENDRITE(-Q)}_a]_n \quad (D)$$

in which the CORE represents an atom or group, n represents an integer of at least 1, Q is a proton or a surface group, a is an integer and DENDRITE, which may be the same or different if n is greater than 1, represents a conjugated dendritic structure comprising aryl and/or heteroaryl groups connected to each other via bonds between sp² hybridised ring atoms of said aryl or heteroaryl groups, CORE terminating in the first single bond which is connected to an sp² hybridised ring atom of an (hetero)aryl group to which more than one conjugated dendritic branch is attached, said atom forming part of the DENDRITE, the CORE and/or DENDRITE being luminescent as well as organometallic dendrimers as disclosed in PCT/GB01/00750 typically those having the formula (E):

$$\text{CORE-[DENDRITE]}_n \quad (E)$$

in which CORE represents a metal ion or a group containing a metal ion, n represents an integer of 1 or more, each DENDRITE, which may be the same or different, represents an inherently at least partially conjugated dendritic molecular structure comprising aryl and/or heteroaryl groups or nitrogen and, optionally, vinyl or acetylenyl groups connected via sp² or sp hybridised carbon atoms of said (hetero)aryl vinyl and acetylenyl groups or via single bonds between N and (hetero)aryl groups, CORE terminating in the single bond which is connected to an sp² hybridised (ring) carbon atom of the first (hetero)aryl group or nitrogen to which more than one at least partially conjugated dendritic branch is attached, said ring carbon atom or N forming part of said DENDRITE, and nitrogen-core containing dendrimers as disclosed in WO01/59030 in general those having the formula (F):

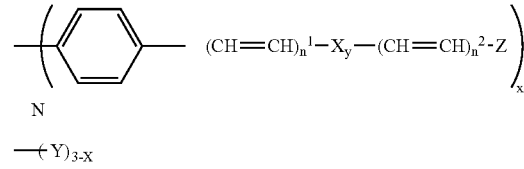

where x is 3, 2 or 1, n¹ and n², which may be the same or different, are 0 or 1 to 3, X represents a divalent mono- or poly-aromatic and/or heteroaromatic moiety, the or each Y, which may be the same or different if x is 1, represents hydrogen or an optionally substituted hydrocarbon group, Z represents an inherently at least partly conjugated dendritic molecular structure comprising aromatic and/or heteroaromatic groups and optionally, alkenylene groups, connected to each other either via a carbon atom of a heteroaromatic group to a ring carbon atom of another (hetero)aromatic group or, if an alkenylene group is present via a ring carbon atom of a (hetero)aromatic group to a carbon atom of an alkenylene group, said dendritic molecular structure being connected to the remainder of the molecule via a ring carbon atom of a (hetero)aromatic group to which more than one at least partly conjugated dendritic chain is attached, one or more of the (hetero)aromatic rings of the dendrimer optionally being substituted, Z and/or the remainder of the molecule, excluding any groups Y, being luminescent, typically x must be 3, to which reference should be made for further details. It will be appreciated that in the case of formula D it is preferred that the reactive unsaturated units are part of the CORE.

Whilst it is preferred that the dendrons and dendrimers formed after modification contain chromophores suitable for opto-electronic applications and, in particular, light-emitting diodes the process of this invention can be used to prepare dendrimers suitable for other applications including dendrimers that have dendrons and/or cores comprised of the basic repeating units of linear polymers but in a branched form. For example, a dendrimer containing phenyl branching points and vinylene linking units as described in WO99/21935 would, once all vinylene units are saturated according to a process of this invention, give a dendritic version of poly (phenyleneethylene). In particular though dendrimers that contain luminescent cores and/or dendrons, and can be used in OLEDs, are preferred. The cores of the dendrimers can be fluorescent or phosphorescent. In the case of fluorescent cores that are only comprised of organic units, i.e. no metal cations, aryl and heteroaryl and fused aryl and heteroaryl and directly linked aryl and heteroaryl systems are preferred. That is the core should not contain unsaturated units that are not aromatic (since otherwise they may react when the non-aromatic unsaturated groups in the dendron are reacted). Examples include phenyl, fluorenyl, thiophenyl, pyridyl and substituted derivatives thereof. Although fluorescent metal complex cores are possible, phosphorescent metal complex cores are preferred. Preferred metal cations that are part of the core are iridium, which is most preferred, rhenium, rhodium, and platinum with the dendrons attached to aryl and nitrogen heteroaryl containing ligands including, for example ligands containing two aromatic groups selected from pyridine, phenyl, benzothiophene, pyrimidinyl, pyrazinyl pyridazinyl, imidazolyl, quinolinyl, isoquinolinyl, naphthyl, anthryl, phenanthryl, benzamidoazolyl, carbazolyl, fluorenyl, pyrazolinyl, oxazolinyl, oxadiazolinyl, triazolyl, triazinyl, thiadiazolyl, benzimidazolyl, benzoxazolyl, furyl, and in particular phenyl-pyridyl and substituted derivatives.

The surface groups of the dendrimers are generally selected so that the dendrimer is soluble in solvents suitable for solution processing, e.g. THF, toluene, chloroform, chlorobenzene, xylenes and alcoholic solvents such as methanol. Suitable groups include those disclosed in WO99/21935. The surface groups can also be chosen such that the dendrimer can be patterned. For example, a cross-linkable group can be chosen, which can be crosslinked upon irradiation or by chemical reaction, as a surface group. Alternatively, the surface groups can comprise protecting groups that can be removed to leave crosslinkable groups. In the case of further reactive surface groups they should be chosen so that they will be stable under the conditions used to react the unsaturated bonds within the dendron or dendrimer. Therefore, vinyl surface groups should generally not be present. The distal groups of the dendrite, to which the surface groups are attached, are aryl or heteroaryl groups. Where t-butyl groups are the surface groups attached to phenyl rings it is preferable that more than one is attached to each of the distal phenyl units.

In a particular embodiment the initial dendrimer is an organometallic dendrimer with a metal cation as part of its core and with at least one dendron which comprises at least one nitrogen atom which forms part of an aromatic ring system or is directly bonded to at least two aromatic groups of the type described in our GB application No. 0206356.8 where the dendron is connected via a vinylene or acetylenyl group of the core. The vinylene or acetylenyl group is then converted into an ethylene group.

In one embodiment the dendrimer is not of the formula:

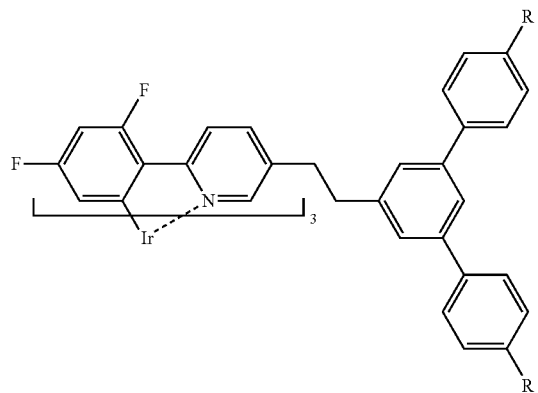

generally having been obtained by hydrogenating a dendron of the formula:

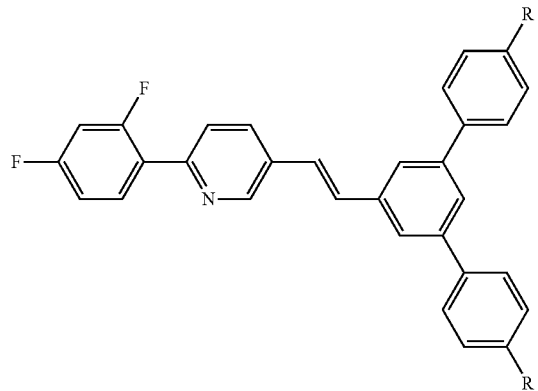

where R is 2-ethylhexyloxy.

Especially the dendron takes the structure

Figure 6:
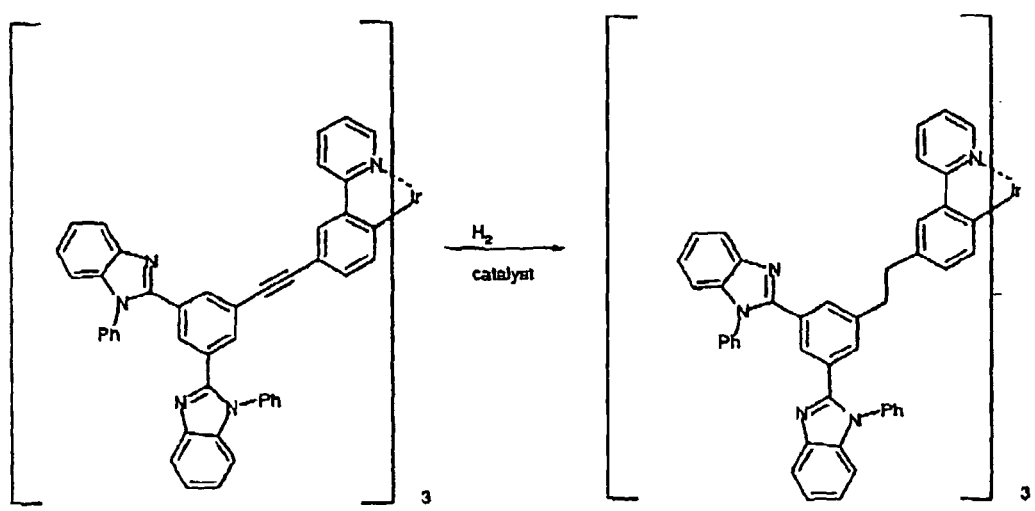
FIG. 6 shows that a preferred dendron has either an acetylenyl or vinyl unit at its foci which can be reacted with, or will become part of the component of, the core wherein the unsaturated bond is reacted to form a saturated link hence disconnecting electronically the core chromophore from unsaturated units in the dendron.

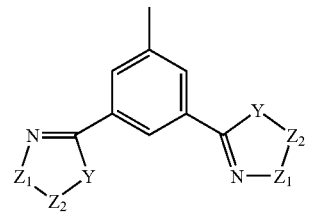

wherein Y is oxygen in which case -$Z_1$-$Z_2$- represents —N=CR$^1$—, or Y is —N—R$^2$ in which case -$Z_1$-$Z_2$ forms part of a benzene ring or —N=CR$^1$, R$^1$ represents an optionally substituted benzene radical and R$^2$ represents an optionally substituted alkyl or aryl group. Thus the nitrogen-containing rings are either oxadiazoles or imidazoles or triazoles. Thus the reaction is typically as shown in FIG. 6. R$^1$ is typically substituted by one or more surface groups, e.g. 3,5-ditertiary butyl. $R^2$ is phenyl, which is preferred, or alkyl, for example of 1 to 15 carbon atoms such as methyl or ethyl; these can be substituted, for example when $R^2$ is phenyl then it can be substituted with, for example, one or more alkyl, alkoxy or halo substituents. These dendrimers form another aspect of the present invention.

The present invention also provides an organometallic dendrimer with a metal cation as part of its core wherein the core is attached directly to the first branching group of at least one dendron by an ethylene or substituted ethylene group.

There are many reactions known in the art that can be carried out on unsaturated bonds; the only restriction is that they must be chemoselective, that is only react with the desired functional group(s). For example, whilst vinylene units can be hydrogenated to give ethylene units, hydrogenation can also be used to cleave benzyl ethers. Therefore, in the case of 4 when the branching group BG is phenyl, hydrogenation has to be carried out so as to react the vinyl (which are the more reactive groups) but not the benzyl ethers. Examples of useful reactions are hydrogenation of vinylene and acetylenyl groups which will give ethylene groups, and the reduction of imines to give amines. It can also be an addition reaction. Vinylenes and acetylenes can also be reacted to give difluoro and tetrafluoro ethylenes. Reaction of vinylenes with diborane (hydroboration) followed by an oxidative work-up can lead to alcohols. The reaction of vinylenes with $HSiCl_3$ in the presence of $H_2PtCl_6$ can give trichloroalkyl silanes (hydrosilylation) which can be further reacted. Vinylenes may also undergo electrophilic addition reactions with hydrogen halides (hydrohalogenation) (HX, e.g. H=Cl or Br) or dihalogens (halogenation)($X_2$) giving monohaloethylenes and dihaloethylenes respectively, while acetylenes will give dihaloethylenes and tetrahaloethylenes. Unsaturated units such as acetylene and vinylene can also undergo cycloaddition reactions although these are less preferred. For example, Diels-Alder reactions and 1,3-dipolar cycloadditions can be used providing that the unsaturated group that has been reacted has less unsaturation between the atoms involved in the original bond than it did before the reaction. All these reactions are well known and those skilled in the art will be well aware of the reaction conditions to employ, in particular if it is desired to be chemoselective.

Figure 7:
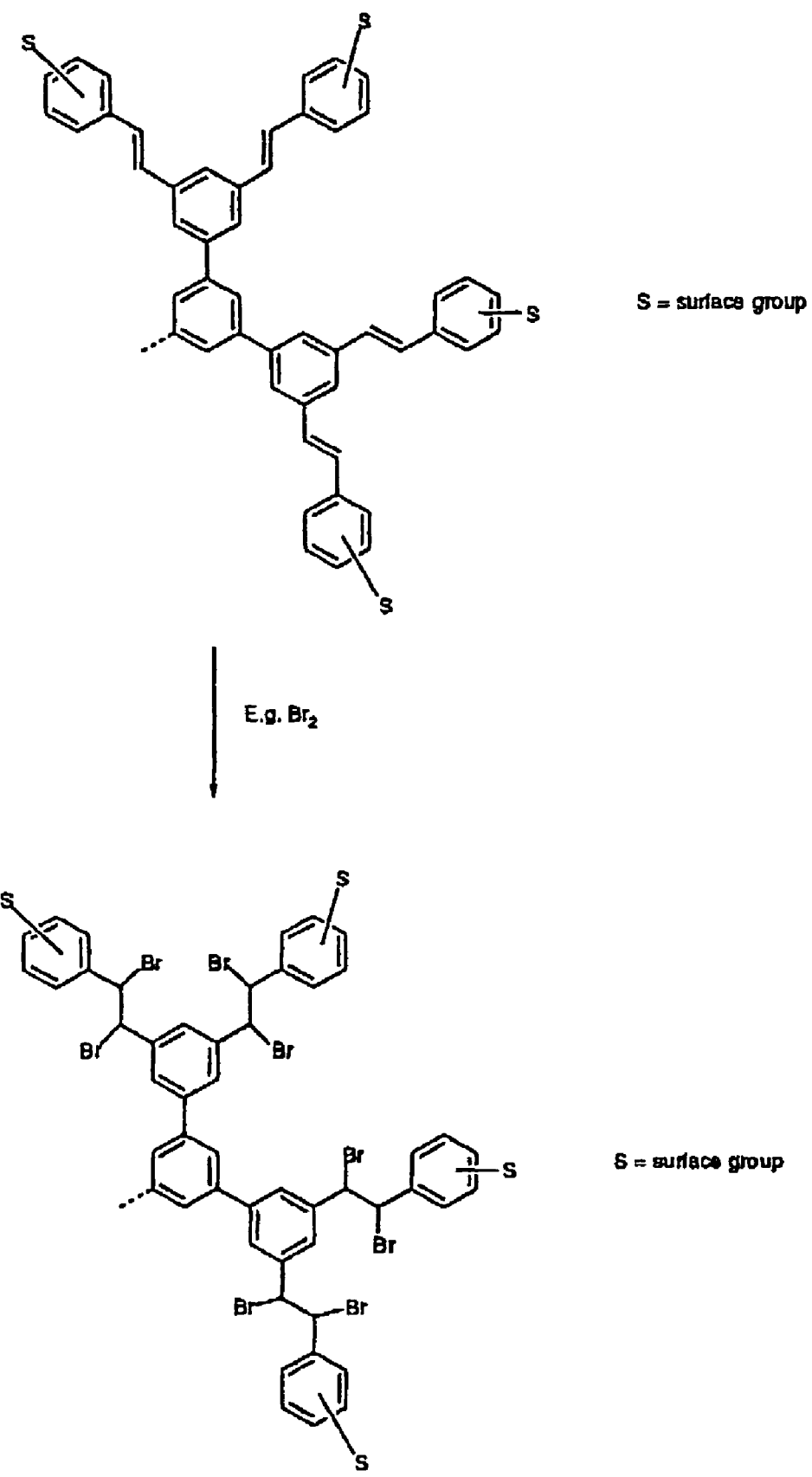
FIG. 7 shows that including one or more unsaturated units in the dendron then, after dendron or dendrimer formation, these units can be converted to reactive groups which can be used in patterning or crosslinking processes, and that preferably the unsaturated unit to be reacted is near the distal end of the dendron or dendrimer.
Figure 8A:
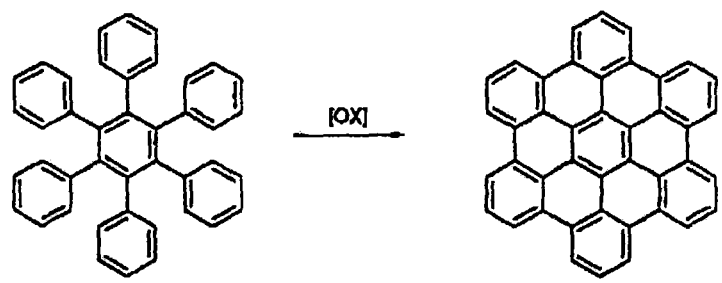
FIG. 8A shows how phenylen based dendrimers can be oxidised to form graphite like structures.
Figure 8B:
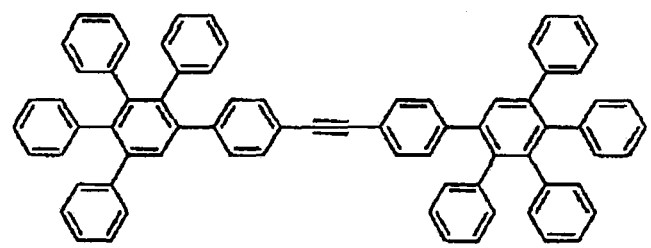
FIG. 8B shows how di-dendroned substituted 4,4-diphenylacetylene dendrons have been cyclised to form larger benzene centered dendrimers.
Figure 8B:
Figure 8B:
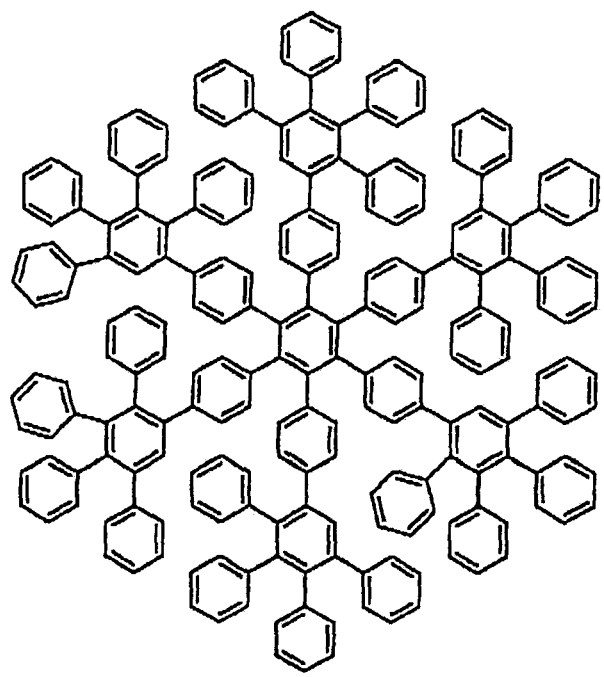

Another advantage of this invention is that not all surface groups which are suitable for synthesis and initial processing are compatible with the chemistry to form the dendrons and/ or dendrimers and still be available for cross-linking and patterning processes. By including one or more unsaturated units in the dendron then, after dendron or dendrimer formation, these units can be converted to reactive groups which can be used in patterning or crosslinking processes. For this aspect of the invention it is preferable that the unsaturated unit to be reacted is near the distal end of the dendron or dendrimer, as shown in FIG. 7.

Figure 3:
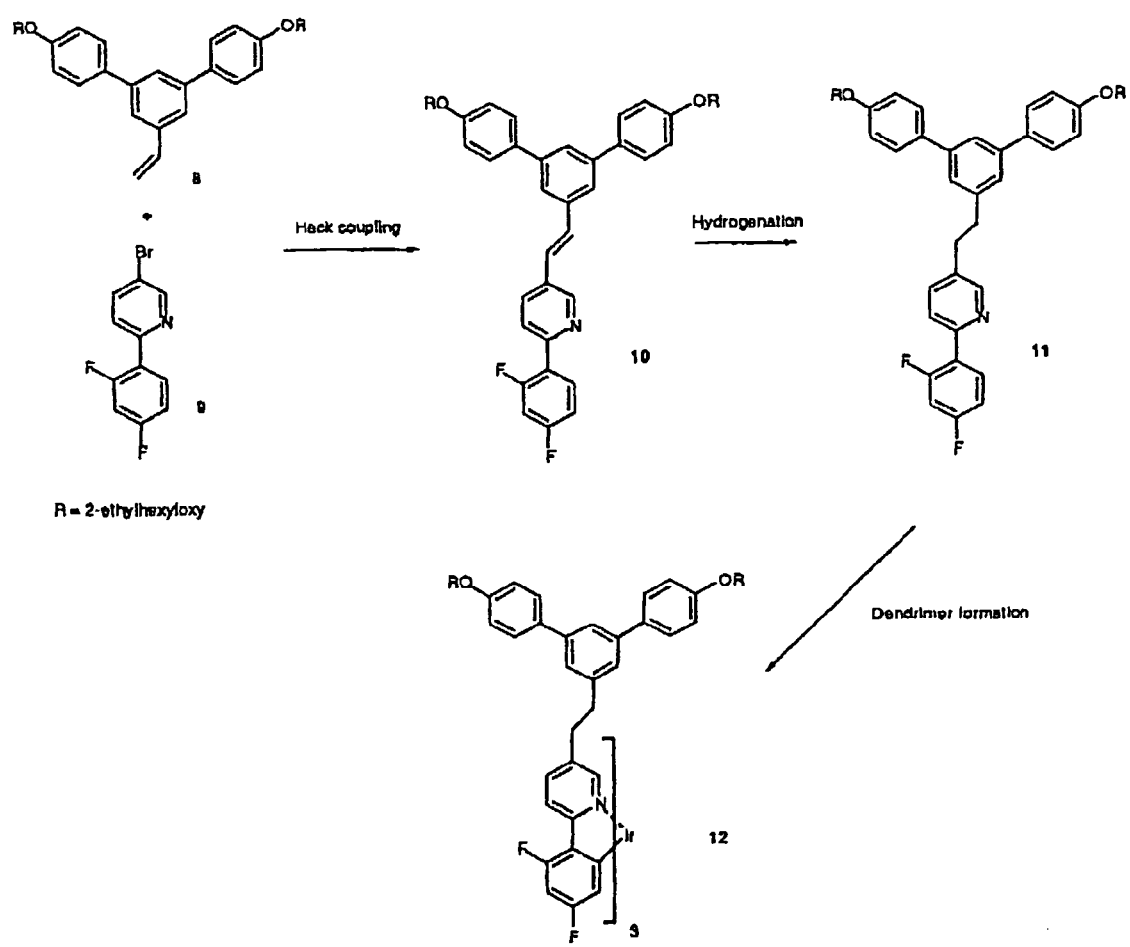
FIG. 3 shows that a preferred dendron has either an acetylenyl or vinyl unit at its foci which can be reacted with, or will become part of the component of, the core wherein the unsaturated bond is reacted to form a saturated link hence disconnecting electronically the core chromophore from unsaturated units in the dendron.

A preferred dendron has either an acetylenyl or vinyl unit at its foci which can be reacted with, or will become part of the component of, the core. This unsaturated bond is then reacted to form a saturated link hence disconnecting electronically the core chromophore from unsaturated units in the dendron, as shown in FIGS. 3 and 6. This can give enhanced control of the colour purity of core emission and can enable the formation of dendrimers which could not be easily synthesised otherwise,—see e.g. FIG. 6.

The properties of dendrimers make them ideal for solution processing. Preferred dendrimers can be dissolved in a solvent, the solution deposited onto a substrate, the solvent removed to leave a solid film. Conventional solution-processing techniques can be used, for example spin-coating, printing (e.g. ink-jet printing) and dip-coating. The resulting solid film is preferably formed on one side of a substrate; the thickness of the solid film is preferably no greater than 2 microns.

The present invention also provides an OLED incorporating a solid film comprising one or more of the dendrimers obtained by the process of this invention. In its simplest form, an organic light-emitting or electroluminescent device can be formed from a light-emitting layer sandwiched between two electrodes, at least one of which is transparent to the emitted light. More commonly there is one or more hole-transporting layers between the anode and the light-emitting layer and/or one or more electron-transporting layers between the light-emitting layer and the cathode.

The present invention then also provides an OLED device comprising layers, in sequence of a substrate, an electrode, a first optional charge-transporting layer, an emissive layer, a second optional charge-transporting layer and a counter electrode, wherein one of the emissive layer or the first or second charge-transporting layers, if present, especially the emissive layer, comprises at least in part of a dendrimer obtained by the process of this invention.

In one embodiment a device according to the invention comprises, at least in part, a dendrimer with a modified dendron and/or core and contains one or more additional species, such as light-emitting dopants, charge-transporting species and/or additional molecular, dendritic and/or polymeric materials.

In one preferred embodiment the film comprising the dendrimer forms the light-emitting layer in an OLED. It is particularly preferred that the dendrimers are the light-emitting species in this light-emitting layer. In an alternative embodiment the film comprising the dendrimer forms a charge-transporting layer in an OLED.

Such a device can have a conventional arrangement comprising a transparent substrate layer, e.g. a glass or PET layer, a transparent electrode layer, a light-emitting layer and a second electrode. The anode, which is generally transparent, is preferably made from indium tin oxide (ITO) although other similar materials including indium oxide/tin oxide, tin oxide/antimony, zinc oxide/aluminium, gold and platinum can also be used, as can conducting polymers such as PANI (polyaniline) or PEDOT/PSS. The cathode is normally made of a low work function metal or alloy such as Al, Ca, Mg, Li or MgAl or optionally with an additional layer of LiF. In an alternative configuration, the substrate may be made of an opaque material such as silicon and light is emitted through the opposing electrode. The OLED devices may be actively or passively addressed.

For a typical OLED device, as described above where the dendrimer is emissive, a solution of the dendrimer can be applied over a transparent electrode layer, the solvent evaporated and then subsequent charge-transporting layers can be applied. The thickness of the dendrimer layer in the OLED is typically 10 nm to 1000 nm, preferably no more than 200 nm, more preferably 30 nm to 120 nm. When a hole transport layer is incorporated between the anode and the emissive dendrimer containing layer the hole transport material must not be removed to a significant extent during the solution deposition.

An OLED device incorporating an emissive layer comprising the dendrimer may optionally have an adjacent first and/or second charge-transporting layer. In our work on dendrimers, it has been found that it is particularly beneficial to have at least one hole-blocking/electron-transporting layer between the light-emitting dendrimer layer and the cathode. Suitable materials for such a hole-blocking/electron-transporting layer are known and include 2,9-dimethyl-4,7-diphenyl-1,10-phenanthroline (BCP), 1,3,5-tris[2-N-phenylbenzimidazolyl)benzene (TPBI), and 2-biphenyl-5(4'-t-butylphenyl) oxadiazole (PBD) aluminium tris(8-hydroxyquinolate) (Alq) and aluminium bis(2-methyl-8-quinolato)-4-phenylphenolate (BAlq). In this, and in other embodiments, the dendrimer-comprising layers may comprise mixtures of two or more dendrimer types, not all of which need be dendrimers of this invention.

Furthermore, additional emissive (fluorescent or phosphorescent) or charge-transporting species may optionally be added to the layer of the dendrimers to improve device characteristics, e.g. efficiency and lifetime. It may further be of benefit to include one or more other molecular and/or dendrimeric and/or polymeric species in the dendrimers to give improved performance. It is preferred that the molecular, dendritic or polymeric species can transport charge in its own right, for example a conjugated polymer or conjugated dendrimer. In one embodiment such additional components form a part of the total blend from 95 to 5 mol %. For example, additional charge-transporting components for use with the light-emitting dendrimers are TPBI, PBD, BCP, 4,4'-bis-(N-carbazolebiphenyl) (CBP), 4,4',4"-tris(N-carbazolyl)triphenylamine (TCTA), and tris-4-(N-3-methylphenyl-N-phenyl) phenylamine (MTDATA).

Such dendrimers can also be used in other device applications such as photovoltaic cells which can contain one or more layers. When used in photovoltaic cells the dendrimer must be capable of absorbing light and/or transporting charge. The dendrimer may be used as a homogeneous layer in a photovoltaic device or blended with other molecular and/or dendritic and/or polymeric materials. Dendrimers may be used in one or more layers of the photovoltaic device. In photovoltaic applications the organometallic dendrimers need not necessarily be charge-neutral.

The Examples that follow further illustrate the present invention.

Example 1

Figure 4:
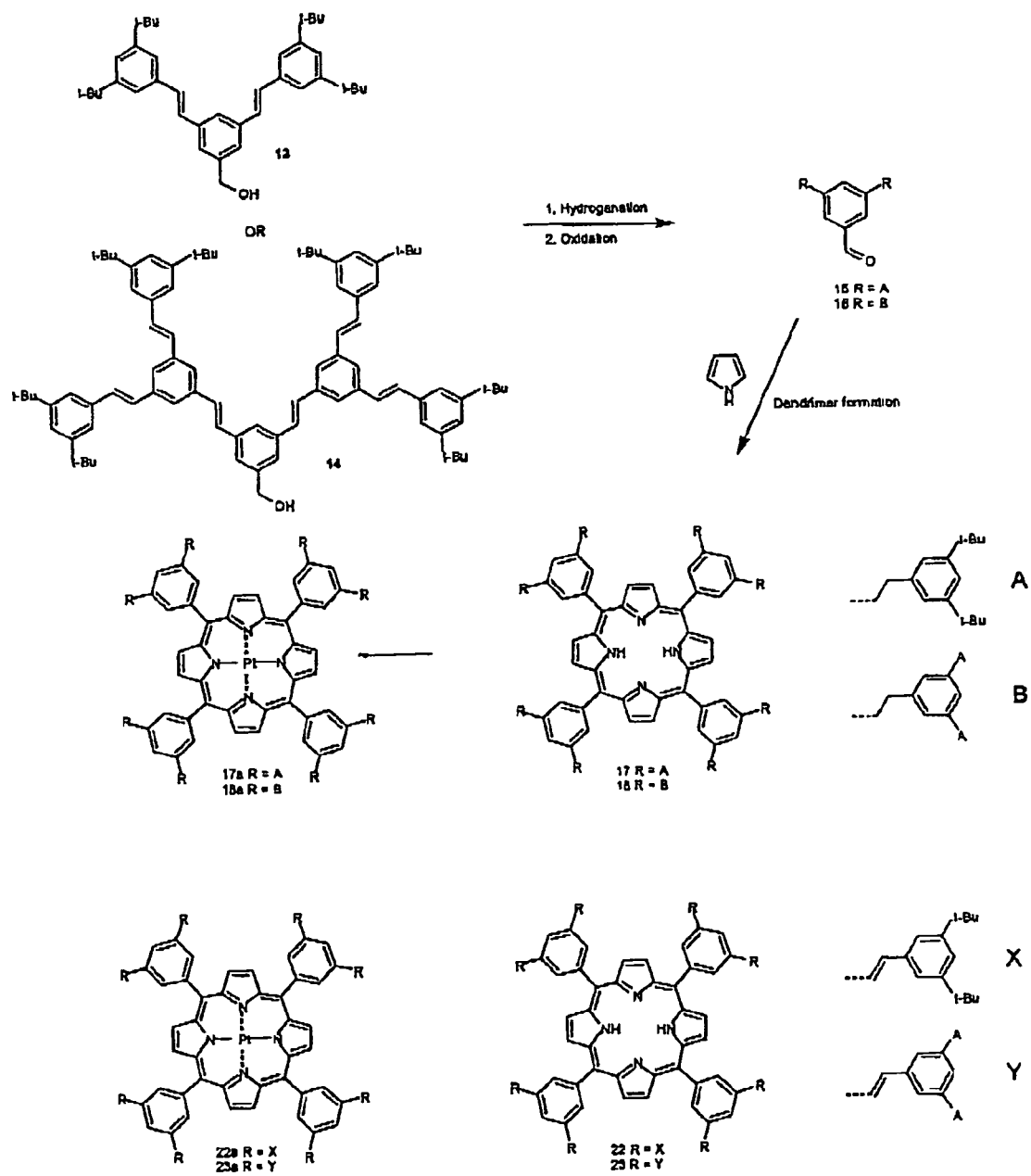
FIG. 4 shows the Example 1 process of modification of stilbene containing dendrons by hydrogenation to form ethylene links between the branching phenyl rings and their subsequent transformation to luminescent dendrimers containing porphyrin cores.

This is illustrated in FIG. 4.

Example 1 describes the process of modification of stilbene containing dendrons by hydrogenation to form ethylene links between the branching phenyl rings and their subsequent transformation to luminescent dendrimers containing porphyrin cores. Example 1 also illustrates the benefit of carrying out the transformation by comparing the photoluminescent quantum yields (PLQY) of dendrimers with porphyrin cores with stilbene and diphenylethane based dendrons (see Table 1).

3,5-Bis[2-(3,5-di-tert-butylphenyl)ethyl)benzaldehyde 15

Hydroxylamine hydrochloride (77.66 g, 1.117 mol) was dissolved in N,N-dimethylformamide (216 cm$^3$). Powdered potassium hydroxide (73.45 g, 1.309 mol) was added and the solution stirred for 10 min, evolving heat and giving a white precipitate. The suspension was filtered, the solid washed with N,N-dimethylformamide (40 cm$^3$) and the filtrates combined and cooled to 0° C. Ethyl acetate (48.6 cm$^3$) was added to give a stock solution which was stirred at 0° C. A suspension of 3,5-bis(3,5-di-tert-butylphenyl-E-vinyl)benzyl alcohol 13 (1.00 g, 1.86 mmol) and stock solution (20 cm$^3$) was heated to 100° C. Stock solution was added in 20 cm$^3$ portions at 20 min intervals with heating maintained at 100° C., and the mixture, which had turned into a homogeneous solution, heated to 100° C. for a further 1 h then allowed to cool. Water (100 cm$^3$) was added and the product extracted into ether (2×100 cm$^3$). The extracts were washed with aqueous hydrochloric acid (3 M, 2×75 cm$^3$) and brine (75 cm$^3$), dried over anhydrous magnesium sulphate, filtered and the solvent removed. The residue was purified by column chromatography over silica with dichloromethane as eluent to leave 3,5-bis[2-(3,5-di-tert-butylphenyl)ethyl)benzylalcohol (957 mg, 95%) as a white solid, mp 101° C. (Found: C, 86.7; H, 10.4. C$_{39}$H$_{56}$O requires C, 86.6; H, 10.4%); $\nu_{max}$ (KBr)/cm$^{-1}$ 3401 (OH) and 1600 (C=C); $\lambda_{max}$(CH$_2$Cl$_2$)/nm 265 (log(ε/dm$^3$mol$^{-1}$cm$^{-1}$) 2.95), 269 sh (2.93), 305 (2.57), 317 (2.56) and 330 sh (3.37); $\delta_H$(400 MHz, CDCl$_3$) 1.34 (36H, s, t-butyl), 1.57 (1H, s, OH), 2.92 (8H, s, CH$_2$CH$_2$), 4.68 (2H, d, J 6, CH$_2$OH), 7.03 (1H, s, bp-H), 7.07 (4H, d, J 2, sp-H), 7.09 (2H, d, J 1, bp-H) and 7.29 (2H, dd, J 2, sp-H); $\delta_C$(100.6 MHz, CDCl$_3$) 31.5, 34.8, 38.3, 38.7, 65.5, 119.9, 122.6, 124.7, 128.1, 140.85, 140.90, 142.6 and 150.7; m/z (APCI$^+$) 523.4 ((M-OH)$^+$, 100%) and 558.4 (MNH$_4^+$, 54%). A solution of 3,5-bis[2-(3,5-di-tert-butylphenyl)ethyl)benzyl alcohol (914 mg, 1.69 mmol) and pyridinium chlorochromate (729 mg, 3.38 mmol) in dichloromethane (4 cm$^3$) was stirred at room temperature for 18 h, the solvent was removed and the residue purified by column chromatography over silica with dichloromethane-light petroleum (2:3) as eluent to leave 15 (902 mg, 99%) as a viscous oil, mp 74-75° C. (Found: C, 86.8; H, 10.1. C$_{39}$H$_{54}$O requires C, 86.9; H, 10.1%); $\nu_{max}$(KBr)/cm$^{-1}$ 1702 (C=O) and 1599 (C=C); $\lambda_{max}$(CH$_2$Cl$_2$)/nm 258 (log (ε/dm$^3$ mol$^{-1}$cm$^{-1}$) 4.18) and 300 (3.45); $\delta_H$(400 MHz, CDCl$_3$) 1.38 (36H, s, t-butyl), 2.95 (8H, m, CH$_2$CH$_2$), 7.03 (4H, d, J 2, sp-H), 7.25 (1H, s, bp-H), 7.30 (2H, dd, J 2, sp-H), 7.57 (2H, s, J 1.5, bp-H) and 9.98 (1H, s, CHO); $\delta_C$(100.6 MHz, CDCl$_3$) 31.5, 34.8, 37.9, 38.4, 120.1, 122.7, 127.5, 135.3, 136.7, 140.2, 143.0, 150.8 and 192.8; m/z (EI$^+$) 538.3 (M$^+$, 18%).

3,5-Bis(2-{3,5-bis[2-(3,5-di-tert-butylphenyl)ethyl] phenyl}ethyl)benzaldehyde 16

A solution of aqueous hydroxylamine (50% w/w, 65.6 cm$^3$, in N,N-dimethylformamide (250 cm$^3$) was cooled over a NaCl—ice bath. Ethyl acetate (46.5 cm$^3$, 0.475 mol) was added and the solution stirred below 0° C. A 25 cm$^3$ portion of this solution was added to a suspension of 3,5-bis[3,5-bis(3, 5-di-tert-butylphenyl-E-vinyl)phenyl-E-vinyl]benzyl alcohol (2.09 g, 1.78 mmol) in toluene (42 cm$^3$) and the mixture heated to 100° C. A homogeneous solution had formed after a few minutes. The remaining hydroxylamine solution was added portionwise over 3 h with stirring maintained at 100° C., and continued at 100° C. for a further 2 h after the addition was complete. The solution was allowed to cool overnight. Water (150 cm$^3$) was added and the mixture extracted with ether (2×150 cm$^3$). The combined extracts were washed with aqueous hydrochloric acid (3 M, 150 cm$^3$), water (150 cm$^3$) and brine (150 cm$^3$), dried over anhydrous magnesium sulphate, filtered and the solvent removed. Analysis of the residue by $^1$H NMR indicated incomplete reduction of the vinyl bonds had occurred. The residue was therefore subjected to the same reaction conditions as above but without the toluene, in the place of the alcohol, to give, upon solvent removal, 3,5-bis(2-{3,5-bis[2-(3,5-di-tert-butylphenyl)ethyl] phenyl}ethyl)benzyl alcohol as a white solid foam (2.105 g, 100%), (Found: C, 88.0; H, 10.3. C$_{87}$H$_{120}$O requires C, 88.4; H, 10.2%); $\nu_{max}$(KBr)/cm$^{-1}$ 1600 (C=C); $\lambda_{max}$(CH$_2$Cl$_2$)/nm 265 (log(ε/dm$^3$ mol$^{-1}$cm$^{-1}$) 3.38), 269 sh (3.36), 306 (3.08), 317 (3.08), and 332 sh (2.87); $\delta_H$(400 MHz, CDCl$_3$) 1.35 (72H, s, t-butyl), 1.61 (1H, t, J 6 CH$_2$OH), 2.91 (24H, s, $CH_2CH_2$), 4.70 (2H, d, J 6, $CH_2OH$), 6.97 (6H, s, G1 bp-H), 7.09 (9H, m, sp-H and cp-H), 7.12 (2H, s, cp-H) and 7.30 (4H, dd, J 2, sp-H); m/z (MALDI) 1204.9 (MNa$^+$, 100%). A solution of 3,5-bis(2-{3,5-bis[2-(3,5-di-tert-butylphenyl)ethyl]phenyl}ethyl)benzyl alcohol (1.317 g, 1.114 mmol) and pyridinium chlorochromate (0.480 g, 2.23 mmol) in dichloromethane (20 cm$^3$) was heated to reflux for 1 h and allowed to cool overnight. The dark brown slurry was then filtered through a plug of silica with dichloromethane as eluent to give 16 (1.29 g, 98%) as a white solid foam, (Found: C, 88.3; H, 10.1. $C_{87}H_{118}O$ requires C, 88.6; H, 10.1%); $\nu_{max}$(KBr)/cm$^{-1}$ 1701 (C=O) and 1600 (C=C); $\lambda_{max}$ ($CH_2Cl_2$)/nm 257 (log($\epsilon$/dm$^3$mol$^{-1}$cm$^{-1}$) 4.12) and 300 (3.43); $\delta_H$(400 MHz, CDCl$_3$) 1.35 (72H, s, t-butyl), 2.90-2.99 (24H, m, $CH_2CH_2$), 6.94 (4H, d, J 1, bp-H), 6.97 (2H, s, bp-H), 7.08 (8H, d, J 2, sp-H), 7.30 (4H, dd, J 2, sp-H), 7.36 (1H, s, cp-H), 7.61 (2H, d, J 1.5, cp-H) and 10.01 (1H, s, CHO); m/z (MALDI) 1202.2 (MNa$^+$, 100%).

5,10,15,20-Tetrakis{3,5-bis[2-(3,5-di-tert-butylphenyl)ethyl]phenyl}porphyrin 17

A solution of 15 (774 mg, 1.44 mmol), pyrrole (99.7 µl, 1.44 mmol) and trifluoroacetic acid (111 µl, 1.44 mmol) in dichloromethane (111 cm$^3$) was stirred in the dark under nitrogen for 9 days 2.5 h. 2,3-Dichloro-5,6-dicyanobenzoquinone (326 mg, 1.44 mmol) was added and the reaction stirred for 20 min, then neutralised by the addition of an excess of sodium bicarbonate (ca. 1.0 g) and filtered through a plug of silica with dichloromethane as eluent. The residue was purified by column chromatography over silica eluting with dichloromethane-light petroleum (1:2), collecting the main band 17 (231 mg, 28%) as a purple solid, mp 215-217° C. (Found: C, 88.0; H, 9.5; N, 2.4; $C_{172}H_{222}N_4$ requires C, 88.1; H, 9.5; N, 2.4%); $\nu_{max}$(KBr)/cm$^{-1}$ 3316 (NH) and 1598 (C=C); $\lambda_{max}$(CH$_2$Cl$_2$)/nm 301 (log($\epsilon$/dm$^3$mol$^{-1}$cm$^{-1}$) 4.23), 374 sh (4.38), 421 (5.81), 517 (4.31), 553 (4.03), 592 (3.80) and 647 (3.76); $\delta_H$(400 MHz, CDCl$_3$)-2.77 (2H, s, NH), 1.32 (144H, s, t-butyl), 3.18 (32H, m, $CH_2CH_2$), 7.16 (16H, d, J 1.5, so H), 7.31 (8H, dd, J 1.5, sp-H), 7.47 (4H, s, bp-H), 7.93 (8H, d, J 1.5, bp-H) and 8.77 (8H, s, β-pyrrolic); m/z (MALDI) 2345.8 (M$^+$, 100%).

5,10,15,20-Tetrakis[3,5-bis(2-{3,5-bis[2-(3,5-di-tert-butylphenyl)ethyl]phenyl}ethyl)-phenyl]porphyrin 18

A solution of 16 (1.22 g, 1.03 mmol), pyrrole (71.5 µl, 1.03 mmol), trifluoroacetic acid (80 µl, 1.0 mmol) and dichloromethane (80 cm$^3$) was stirred under argon in the dark for 6 days 19 h. 2,3-Dichloro-5,6-dicyanobenzoquinone (234 mg, 1.03 mmol) was added and the reaction stirred for 5 min, then neutralised by the addition of diethylamine (2 cm$^3$), filtered through a plug of silica with dichloromethane as eluent and the solvent removed. The residue was purified by column chromatography over silica with dichloromethane-light petroleum as eluent. The product was precipitated from a dichloromethane solution by the addition of methanol and dried under vacuum to leave 18 (207 mg, 16%) as a foamy purple solid, (Found: C, 88.5; H, 9.5; N, 1.2. $C_{364}H_{478}N_4$ requires C, 89.1; H, 9.8; N, 1.1%); $\nu_{max}$(KBr)/cm$^{-1}$ 1599 (C=C); $\lambda_{max}$(CH$_2$Cl$_2$)/nm 302 (log($\epsilon$/dm$^3$mol$^{-1}$cm$^{-1}$) 4.40), 373 (4.50), 421 (5.80), 517 (4.35), 551 (4.14), 593 (3.83) and 651 (4.16); $\delta_H$(400 MHz, CDCl$_3$)-2.64 (2H, s, NH), 1.26 (288H, s, t-butyl), 2.88 (64H, s, G2 ethyl H), 3.13 (32, m, G1 ethyl H), 6.94 (8H, s, bp-H), 7.02 (48H, m, sp-H bp-H), 7.22 (16H, dd, J 1.5, sp-H), 7.51 (4H, s, cp-H), 8.04 (8H, d, J 2, cp-H) and 8.98 (8H, s, β-pyrrolic); m/z (MALDI) 4910.9 (M$^+$, 100%).

5,10,15,20-Tetrakis{3,5-bis[2-(3,5-di-tert-butylphenyl)ethyl)phenyl}porphinato platinum (II) 17a 5,10,15,20-Tetrakis {3,5-bis[2-(3,5-di-tert-butylphenyl)ethyl]phenyl}porphine 17 (150 mg, 63.9 µmol) was added to a refluxing solution of platinum (II) chloride (34.0 mg, 0.128 mmol) in benzonitrile (2 cm$^3$), washing in with benzonitrile (1.0 cm$^3$) and the mixture heated to reflux under nitrogen for 21 h. The benzonitrile was removed and the residue was purified by column chromatography over silica with dichloromethane-light petroleum (2:3) as eluent and the orange solid recrystallised from a dichloromethane-methanol mixture to give 17a (143 mg, 88%) as orange crystals, mp 128° C. (Found: C, 81.3; H, 8.7; N, 2.2. $C_{172}H_{220}N_4Pt$ requires C, 81.4; H, 8.7; N, 2.2%); $\nu_{max}$(KBr)/cm$^{-1}$ 1598 (C=C); $\lambda_{max}$ (CH$_2$Cl$_2$)/nm 293 (log($\epsilon$/dm$^3$mol$^{-1}$cm$^{-1}$) 3.99), 405 (5.68), 511 (4.60) and 540 (3.79); $\delta_H$(400 MHz, CDCl$_3$) 1.32 (144H, s, t-butyl), 3.15 (32H, m, ethyl H), 7.15 (16H, d, J 2, sp H), 7.31 (8H, dd, J 2, sp H), 7.45 (4H, s, bp H), 7.87 (8H, d, J 1.5, bp H) and 8.68 (8H, s, β-pyrrolic H); m/z (MALDI) 2537.7 (M$^+$, 100%).

5,10,15,20-Tetrakis[3,5-bis(2-{3,5-bis[2-(3,5-di-tert-butylphenyl)ethyl]phenyl}ethyl)phenyl]porphyrinato platinum (II) 18a 5,10,15,20-Tetrakis[3,5-bis(2-{3,5-bis[2-(3,5-di-tert-butylphenyl)ethyl]phenyl}-ethyl)phenyl]porphine 18 (273 mg, 0.056 mmol) was added to a refluxing solution of platinum (II) chloride (54.0 mg, 0.203 mmol) in benzonitrile (1 cm$^3$) and the solution heated to reflux under a fast stream of nitrogen for 3.5 h. The benzonitrile was removed and the residue purified by column chromatography over silica with dichloromethane-light petroleum (1:4) as eluent to leave 18a (213 mg, 75%) as an orange solid, mp 92-93° C. (Found: C, 84.5; H, 9.9; N, 1.18. $C_{364}H_{476}N_4Pt$ requires C, 85.7; H, 9.4; N, 1.1%); $\nu_{max}$(KBr)/cm$^{-1}$ 1599 (C=C); $\lambda_{max}$(CH$_2$Cl$_2$)/nm 295 (log($\epsilon$/dm$^3$mol$^{-1}$cm$^{-1}$) 4.32), 405 (5.53), 511 (4.47) and 540 (3.45); $\delta_H$(400 MHz, CDCl$_3$) 1.26 (288H, s, t-butyl), 2.88 (64H, s, G2 ethyl H), 3.13 (32, m, G1 ethyl H), 6.93 (8H, s, bp H), 7.02 (48H, m, sp H and G2-bp H), 7.23 (16H, dd, J 1.5, sp H), 7.49 (4H, s, G1-bp H), 7.98 (8H, d, J 1, G1-bp H) and 8.89 (8H, s, β-pyrrolic H); m/z (MALDI) 5103.8 (MH$^+$, 100%).

The PLQY of the free-base and platinum chelated porphyrins with the dendrons containing the unsaturated vinylene bonds between the phenyl branching points (stilbene) and equivalent dendrimers but with the vinylene units converted to saturated ethylene units were measured and the results are shown in Table 1.

TABLE 1

| | Stilbene | | | Saturated | |
|---|---|---|---|---|---|
| Compound | PLQY in THF (%) | Film PLQY (%) | Compound | PLQY in THF (%) | Film PLQY (%) |
| 22 | 12 | 1.7 | 17 | 13 | 0.8 |
| 23 | 10 | 1.8 | 18 | 11 | 4.8 |
| 22a | 9 | 0.84 | 17a | 16 | 2.2 |
| 23a | 4 | 0.91 | 18a | 16 | 2.6 |

Luminescence efficiency was generally enhanced upon hydrogenation of the stilbenes. For the vinylene porphyrins 22 and 23, the film PLQY was less than 20% of the solution PLQY. By hydrogenation to give dendrimer 18, the film PLQY was improved to 44% of the solution PLQY. In 17 the lower (first) generation dendrons do not give as good an isolation of the core, so the film PLQY is still low. For the platinum porphyrin stilbene dendrimers 22a and 23a, the solution PLQY was low and decreased with increasing generation. For the platinum porphyrin dendrimers 17a and 18a with ethylene links in the dendrons, the solution PLQY were higher and did not decrease with increasing generation. The film PLQY for 17a and 18a was also three times higher than that for 22a and 23a showing the improvement in PLQY on removing the unsaturation in the dendrons.

Example 2

Figure 5:
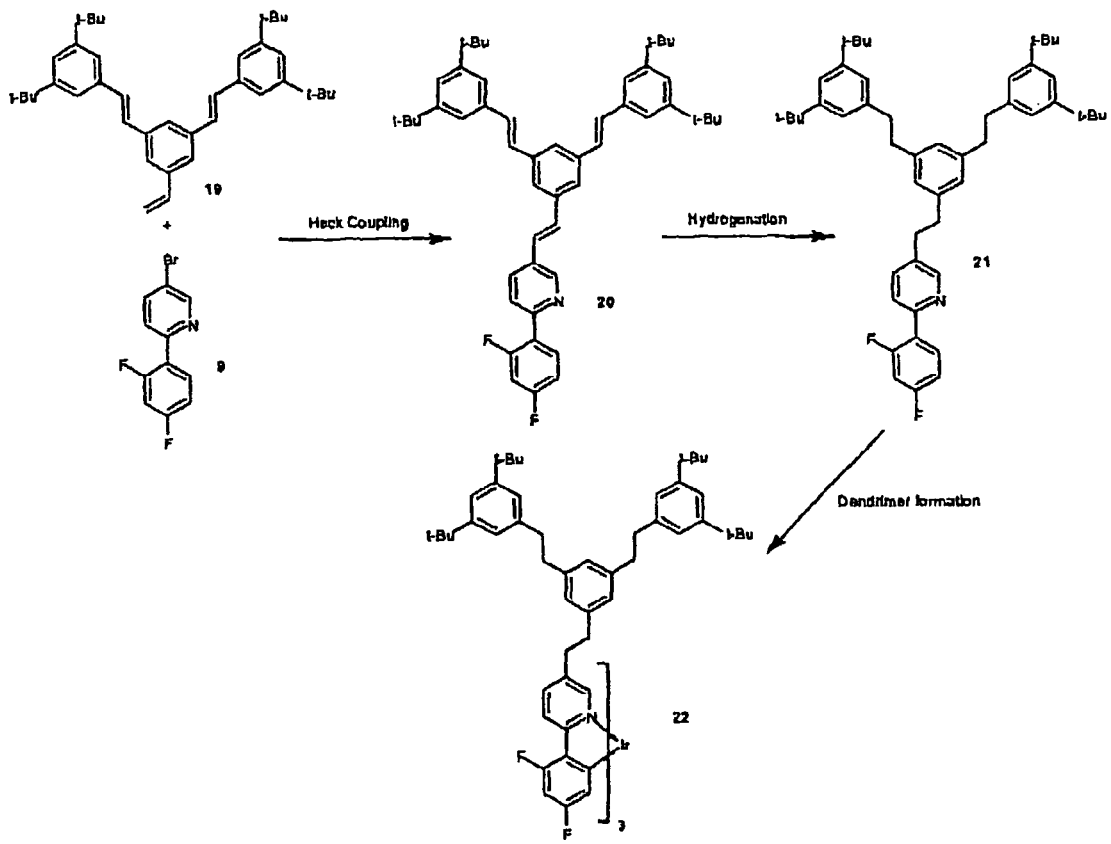
FIG. 5 shows the Example 2 process for the formation of a dendrimer with an iridium cation as part of its core and saturated units formed by hydrogenation of vinylene units.

This is illustrated in FIG. 5 and shows the process for the formation of a dendrimer with an iridium cation as part of its core and saturated units formed by hydrogenation of vinylene units.

2-(2',4'-difluorophenyl)-5-[3",5"-bis(3''',5'''-di-tert-butylstyryl)styryl]pyridine 20

A mixture of 3,5-bis(3',5'-di-tert-butylstyryl)styrene 19 (2.161 g, 4.06 mmol), 2-(2',4'-difluorophenyl)-5-bromopyridine 9 (997 mg, 3.69 mmol), sodium carbonate (430 mg, 4.06 mmol), di-tert-butylcresol (407 mg, 1.85 mmol), trans-di(μ-acetato)-bis[o-(di-o-tolylphosphino)benzyl]dipalladium (II) (174 mg, 0.185 mmol) and N,N-dimethylacetamide (50 cm³) was deoxygenated by alternate exposure to high vacuum and argon, then heated at 130° C. for 21 hours. Water (100 cm³) and dichloromethane (100 cm³) were added. The aqueous layer was separated and extracted with dichloromethane (3×50 cm³). The combined organic layers were washed with water (5×200 cm³), brine (200 cm³), dried over magnesium sulfate and the solvent removed. The crude product was purified by column chromatography over silica using ethyl acetate/light petroleum (1:8) as the eluent. The main band was isolated and the solvent completely removed to give an orange oil. This was recrystallized from dichloromethane/methanol to leave an orange solid of 20 (810 mg, 30%), mp 230-233° C., found 722.4540. $C_{51}H_{58}NF_2$ requires 722.4537; $\nu_{max}$(Nujol)/cm$^{-1}$ 1594 (C=C); $\delta_H$(400 MHz, CDCl$_3$) 1.39 (36H, s, t-Bu), 6.95 (1H, m, 6'-H), 7.04 (1H, m, 5'-H), 7.21 (1H, s, 4-H), 7.27 (2H, s, 8'''-H), 7.28 (2H, s, 7'''-H), 7.33 (1H, s, 3-H), 7.41 (2H, t, J 1.7, 4''''-H), 7.45 (4H, d, J 1.7, 2''', 6'''-H), 7.64 (2H, d, J 1.1, 2", 6"-H), 7.68 (1H, s, 4"-H), 7.82 (1H, dd, J 6, J' 1.1, 7"-H), 7.97 (1H, dd, J 6, J' 2, 8"-H), 8.09 (1H, td, J 11, J 8, 3'-H), 8.87 (1H, d, J 2, 6-H); m/z (APCI$^+$) 720 (MH$^+$, 100%).

2-(2',4'-difluorophenyl)-5-[2"-(3''',5'''-bis[2''''-(3''''',5'''''-di-tert-butylphenyl)ethyl]phenyl)ethyl]pyridine 21

A mixture of 20 (668 mg, 0.925 mmol), 5% palladium on carbon (100 mg, 0.046 mmol) and tetrahydrofuran was deoxygenated and stirred under hydrogen (1 atm) for 17 hours. The mixture was filtered through Celite® using ether as eluent, and the solvent was removed to leave a brown oil. The crude product was purified by column chromatography over silica using ethyl acetate-light petroleum (1:15) as the eluent. The main band was isolated and the solvent completely removed to give 21 (550 mg, 82%) as a pale oil, MH$^+$ found 728.5007; $C_{51}H_{64}NF_2$ requires 728.5007; $\delta_H$(400 MHz, CDCl$_3$) 1.34 (36H, s, t-Bu), 2.89 (8H, s, CH$_2$), 2.9-3.0 (4H, m, CH$_2$), 6.85-7.05 (5H, m, 5', 6', 2", 4", 6"-H), 7.06 (4H, d, J 1.8, 2''', 6'''-H), 7.29 (2H, t, J 1.7, 4''''-H), 7.54 (11H, dd, J 8, J' 2.2, 4-H), 7.58 (1H, dd, J 8, J' 2.2, 3-H), 7.99 (1H, td, J 11, J 8, 3'-H), 8.55 (1H, d, J 1.8, 6-H); m/z (APCI$^+$) 728 (MH$^+$, 100%).

Tris[3,5-difluoro-2-(5'-[2"-(3''',5'''-bis[2''''-(3''''',5'''''-di-tert-butylphenyl)ethyl]phenyl)ethyl]pyridinyl) phenyl-C,N]-iridium 22

A mixture of 21 (177 mg, 0.24 mmol), iridium trichloride trihydrate (34 mg, 0.097 mmol), water (1 cm³) and ethoxyethanol (3 cm³) was degassed, then stirred and heated at reflux under argon for 18 hours. Water was added until a yellow precipitate formed. This was filtered off, dissolved in dichloromethane, filtered and the solvent removed to leave a yellow solid. The crude product was passed through a plug of silica using ethyl acetate-light petroleum (1:8) as the eluent to remove baseline impurities, to leave a yellow solid (130 mg). A mixture of the yellow solid (122 mg), 21 (280 mg, 0.385 mmol) and silver triflate (9 mg, 0.0363 mmol) was heated at 150° C. under argon for 24 hours. The crude mixture was separated by column chromatography over silica using dichloromethane-light petroleum (1:4) as the eluent to give 22 (40 mg, 23%), yellow solid, mp 86-92° C.; $\delta_{max}$(CH$_2$Cl$_2$)/nm 276 (log($\epsilon$/dm³mol$^{-1}$cm$^{-1}$) 4.67), 346 (4.09), 381 sh (3.85); $\delta_H$(400 MHz, CDCl$_3$) 1.28 (108H, s, t-Bu), 2.6-2.7 (12H, m, CH$_2$), 2.80 (24H, s, CH$_2$), 6.28 (3H, dd, J 9, J' 2.4, 5'-H), 6.39 (3H, m, 3'-H), 6.71 (6H, d, J 1, 2", 6"-H), 6.86 (3H, s, 4"-H), 7.01 (12H, d, J 1.7, 2''', 6'''-H), 7.27 (6H, m, 4''''-H), 7.30 (3H, d, J 1.7, 3-H), 7.43 (3H, dd, 4-H), 8.20 (3H, dd, 6-H); m/z (MALDI) 2373 (M$^+$, 100%).

The invention claimed is:

1. A process for modifying at least one dendron intended to form part of a dendrimer, said dendron having the formula:

FO(dendrite-$Q_a$)$_y$ wherein FO is a functional group attached, either directly or via a linking group which can contain one or more reactable unsaturated units, to the first branching atom or group of the dendrite, each "dendrite" which may be the same or different is a dendrite which contains branching atoms or groups and optionally linking groups and comprises at least said first branching atom or group which must have, in addition to FO, 2 or more groups attached and in which the distal group of each arm of the dendrite is an aryl or heteroaryl group, at least one of said dendrite or, if present, the linking group to FO containing one or more reactable unsaturated units, y is 1 or more, Q is a surface group and a is 0 or an integer, which comprises reacting at least one said reactable unsaturated group in a chemoselective manner to form a less unsaturated group, with the proviso that the process does not comprise hydrogenating a dendron of the formula

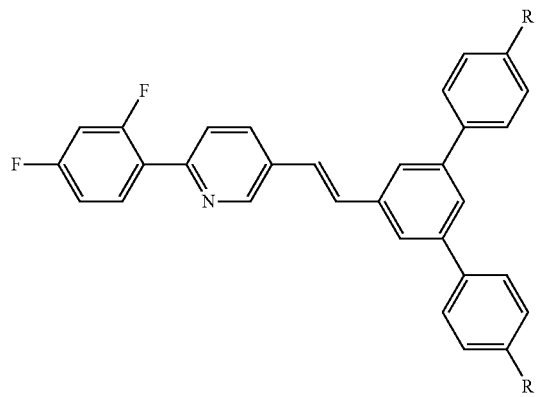

where R is 2-ethylhexyloxy.

2. A process for modifying a dendrimer of the formula:

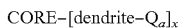

wherein Q and a are as defined above, x is one or 2 or more such that when x is more than one each dendrite–Qa can be the same or different and CORE represents an atom or group and CORE terminates at the single bond to the first branching atom or group in the or each "dendrite", each "dendrite" which may be the same or different and is a dendrite which contains branching atoms or groups and optionally linking groups, at least one of CORE and dendrite comprising at least one reactable unsaturated group, provided that the distal group of each arm of the or each dendrite is an aryl or heteroaryl group, which comprises reacting at least one reactable unsaturated group to form a less unsaturated group in a chemoselective manner.

3. A process according to claim 2 wherein the reactable unsaturated group becomes fully saturated.

4. A process according to claim 2 wherein only linking groups are reacted.

5. A process according to claim 2 wherein the reactable unsaturated group is a vinylene or acetylenyl group.

6. A process according to claim 2 where the first branching point in the dendrite is a (hetero)aryl group or fused (hetero)aryl group.

7. A process according to claim 6 wherein all the branching points in the dendrite are aryl, heteroaryl or fused (hetero)aryl.

8. A process according to claim 2 wherein the first branching point in the dendrite is a 1,3,5-substituted phenyl group or a 3,6-N-substituted carbazole group.

9. A process according to claim 2 wherein the reactable unsaturated group is part of the core and directly bonded to the first branching group of a dendrite.

10. A process according to claim 2 wherein the dendrimer is asymmetric.

11. A process according to claim 2 wherein the dendrimer is an organometallic dendrimer.

12. A process according to claim 2 wherein the group which has been reacted by a chemoselective reaction is subsequently reacted further.

13. A process according to claim 2 wherein the chemoselective reaction is an addition reaction.

14. A process according to claim 2 wherein the chemoselective reaction is a hydrogenation.

15. A process according to claim 2 wherein the chemoselective reaction involves hydrohalogenation, halogenation, hydrosilylation or hydroboration followed by oxidation.

16. A process according to claim 2 wherein the chemoselective reaction is a cycloaddition.

17. A process according to claim 2 wherein the said reactable unsaturated group is part of a dendrimer that has one at least inherently partially conjugated dendrite.

18. A process according to claim 2 wherein the said reactable unsaturated group is part of a dendrimer that comprises more than one at least inherently conjugated dendrite and the dendrites are attached to at least two ligands complexed to the metal cation which forms part of the core and the chemoselective reaction takes place in the core.

19. A process according to claim 2 wherein the dendrimer has one or more surface groups which allows patterning.

20. A process according to claim 2 wherein the film is capable of emitting visible light.

21. A process for making a dendrimer which involves reacting at least one dendron with a dendrimer precursor wherein the dendron is one which has been modified by a process as claimed in claim 1.

22. A dendron or dendrimer whenever obtained by a process as claimed in claim 2.

23. An organic light emitting device comprising, in sequence, layers of a substrate, an electrode, a first optional charge-transporting layer, a light emissive layer, a second optional charge-transporting layer and a counter electrode, wherein at least one of the emissive layer, first optional charge-transporting layer and second optional charge-transporting layers is a film of a dendrimer as claimed in claim 22.

24. A device according to claim 23 wherein the emissive layer is a film of a dendrimer.

25. A device according to claim 24 which comprises at least one charge-transporting layer.

26. A dendrimer of claim 22 in a photovoltaic device.

* * * * *